United States Patent [19]

Antrim et al.

[11] Patent Number: 5,001,063
[45] Date of Patent: Mar. 19, 1991

[54] TREATMENT OF CELLULOSIC ION EXCHANGE COMPOSITES IN HOT AQUEOUS MEDIUM TO INCREASE ADSORPTION OF MACROMOLECULES

[75] Inventors: Richard L. Antrim, Sparta, N.J.; Donald W. Harris, Decatur, Ill.

[73] Assignee: Cultor, Ltd., Helsinki, Finland

[21] Appl. No.: 196,152

[22] Filed: May 19, 1988

Related U.S. Application Data

[63] Continuation-in-part of Ser. No. 694,867, Jan. 25, 1985, abandoned.

[51] Int. Cl.$^5$ .................. C12N 11/12; C12N 9/92; C08B 15/00
[52] U.S. Cl. .................... 435/179; 435/176; 435/180; 435/234; 435/815; 530/814; 536/56
[58] Field of Search ............ 435/174, 179, 180, 182, 435/234, 815; 530/814; 536/56; 521/28

[56] References Cited

U.S. PATENT DOCUMENTS

| | | | |
|---|---|---|---|
| 3,234,199 | 2/1966 | Reid | 435/815 X |
| 3,634,394 | 1/1972 | Andreassen | |
| 4,110,164 | 8/1978 | Sutthoff et al. | 435/182 X |
| 4,168,250 | 9/1979 | Sutthoff et al. | 435/179 X |
| 4,205,127 | 5/1980 | Fujita et al. | 435/179 |
| 4,355,117 | 10/1982 | Antrim et al. | 435/179 X |

FOREIGN PATENT DOCUMENTS

| | | | |
|---|---|---|---|
| 31075 | 10/1979 | Japan | 435/179 |
| 896439 | 5/1962 | United Kingdom . | |
| 1435396 | 5/1976 | United Kingdom . | |

*Primary Examiner*—David M. Naff
*Attorney, Agent, or Firm*—Scully, Scott, Murphy & Presser

[57] ABSTRACT

A composite containing DEAE-cellulose agglomerated with a hydrophobic polymer is treated with tap water, deionized water or a dilute salt solution at a temperature of at least 60° C. for a time sufficient to increase adsorption capacity for charged macromolecules by at least about 30%. Treatment is preferably at a temperature of about 80° to about 100° C. for a time period of about one-half hour to about 5 hours. The macromolecule is preferably a protein such as the enzyme, glucose isomerase.

57 Claims, No Drawings

TREATMENT OF CELLULOSIC ION EXCHANGE COMPOSITES IN HOT AQUEOUS MEDIUM TO INCREASE ADSORPTION OF MACROMOLECULES

CROSS REFERENCES TO RELATED PATENT APPLICATIONS

This patent application is a continuation-in-part of U.S. application Ser. No. 694,867 filed Jan. 25, 1985.

FIELD OF THE INVENTION

This invention relates to the field of enzyme immobilization. More specifically, the invention provides a process for increasing the adsorption capacity of granular derivatized cellulosic ion exchange composites and the improved product produced thereby.

BACKGROUND OF THE INVENTION

In food processing and other commercial applications, the use of microbial or fungal enzymes adsorbed onto or bonded to inert carriers to provide immobilized biological catalysts has largely superseded older methods wherein soluble enzymes or whole cells of microorganisms were utilized. In general, the use of immobilized enzymes provides a number of significant advantages over the older methods. The major advantage is that the immobilized enzymes are adaptable for use in continuous conversion processes. Thus, a more efficient use of the enzyme is attained and the contact time between the enzyme and the substrate is reduced, thereby resulting in an improved product quality and a reduction in enzyme and production costs.

Cellulose occurs in nature as a linear polymer comprised of anhydroglucose units joined together by $\beta$-1,4 glucosidic bonds. Each anhydroglucose unit contains three free hydroxyl groups capable of reacting with appropriate reagents to form insoluble cellulose derivatives which, due to their inertness, large surface area, and open, porous structure, have a high adsorptive or ion-exchange capacity for protein molecules.

The preparation and utilization of ion exchange enzyme adsorbents derived from cellulose are known in the art. Peterson and Sober, J. A. C. S. 78, 751 (1956) and Guthrie and Bullock, I/EC, 52, 935 (1960) described methods for preparing adsorptive cellulose products which could be utilized to separate or purify enzymes and other proteins. Tsumura et al., Nippon Shakuhin Kogyo Gakkaishi, 14, (12), (1967) disclosed binding glucose isomerase to DEAE-Sephadex.

U.S. Pat. No. 3,708,397 to Sipos relates to a process for immobilizing glucose isomerase on basic anion exchange celluloses. U.S. Pat. No. 3,823,133 to Hurst et al. is directed to a method for preparing cationic cellulose ethers having a high adsorptive capacity for enzymes and other proteinaceous materials. U.S. Pat. No. 3,838,007 to van Velzen sets forth a process in which an enzyme preparation is obtained in particulate form. U.S. Pat. Nos. 3,788,945 and 3,909,354, both to Thompson et al., disclose continuous processes for converting glucose to fructose by passing a glucose-containing solution through fixed or fluidized beds containing glucose isomerase bound to various cellulose products. U.S. Pat. No. 3,947,325 to Dinelli et al. is directed to the preparation of cellulose-containing englobed enzymatic material. The cellulose is formed from an emulsion comprising an aqueous enzyme solution and nitrocellulose. U.S. Pat. No. 3,956,065 to Idaszak et al. is concerned with a continuous process for converting glucose to fructose whereby a glucose-containing solution is passed through a bed comprising a cellulose derivative having glucose isomerase immobilized thereon and non-porous or granular polystyrene beads. The beads inhibit packing and channeling of the bed when such is used in flow reactors. Peska et al., in an article entitled "Ion Exchange Derivatives of Bead Cellulose", Die Angewandte Makromolekulare Chemie, 53, pp. 73–80, (1976), described several derivatized celluloses prepared in bead form.

U.S. Pat. Nos. 4,110,164 and 4,168,250, both to Sutthoff et al., relate to agglomerated fibrous ion exchange cellulose composites and processes for preparing the same. In these processes a hydrophobic polymer is combined with fibrous (rather than granular) cellulose which has previously been derivatized to impart ion exchange properties thereto. Although these composites perform satisfactorily in a number of applications, their ion exchange capability and capacity for adsorbing or binding glucose isomerase are not as great as desired. Moreover, the economics of these processes are such as to make the production of the composites more costly than is preferred.

U.S. Pat. No. 4,355,117 to Antrim et al. provides a process for preparing an agglomerated DEAE-cellulose composite which overcomes many of the shortcomings discussed above and is the preferred process for preparing the composite useful in practicing this invention.

U.S. Pat. Nos.4,205,127 to Fujita et al. teaches the use of an aqueous salt solution at 50°–75° C. to desorb spent enzyme from synthetic anion exchange resins such as styrene-divinyl benzene resin (Column 1, lines 39–59). Fujita does not disclose the use of any cellulosic resins.

Japanese patent publication 31075/1979 teaches that DEAE-cellulose may be used as a support for glucoamylase. The enzyme is added to the support from an aqueous solution until swelling equilbrium is reached.

U.S. Pat. No. 3,234,199 to Reid uses a mixture of cationic and anionic exchange resins in a protein fractionation process. None of the Reid resins are cellulosic. Further, Reod washes his resins so as to specifically avoid the use of elevated temperatures (Column 3, lines 49–52).

BRIEF DESCRIPTION OF THE INVENTION

This invention provides an improved process for preparing an agglomerated DEAE-cellulose composite capable of adsorbing or binding charged macromolecules wherein a DEAE-cellulose is first agglomerated with a hydrophobic polymer to form a granular composite, and then the resulting composite is then treated with an aqueous medium at elevated temperature and for sufficient time to increase the adsorption or binding capacity of the composite.

This invention further provides a process for increasing the adsorption or binding capacity of a granular DEAE-cellulose composite for charged macromolecules comprising:

(a) agglomerating a cellulose with a hydrophobic polymer to form a granular composite;

(b) derivatizing the agglomerated cellulose in the composite with a derivatizing agent to impart ion exchange properties thereto, at least a portion of the derivatized cellulose being free to adsorb charged macromolecules;

(c) maintaining the derivatized composite in granular form; and (d) treating the granular derivatized composite with an aqueous medium at an elevated temperature for a sufficient period of time to increase the macromolecular adsorption capacity of the derivatized composite.

DETAILED DESCRIPTION OF THE INVENTION

Cellulose can be derivatized to provide ion exchange materials having high loading capacities in regard to adsorbing or immobilizing macromolecules. For this purpose, the cellulose may be derivatized to provide ion exchange materials having either anion or cation exchange capabilities, depending upon the charge present on the material adsorbed. When the material to be adsorbed is glucose isomerase, the cellulose will advantageously be derivatized to the anion exchange form since in this form its loading capacity for this enzyme is extremely high. Typically, to produce the anion exchange form the agglomerated cellulose will be treated with appropriate reagents to form, among others, the di-and tri-ethyl-aminoethyl celluloses, such as DEAE-cellulose and TEAE-cellulose, and the cellulose derivatives of epichlorohydrin and triethanolamine, such as ECTEOLA-cellulose. Background information and methods for derivatizing cellulose are disclosed in U.S. Pat. No. 3,823,133 to Hurst et al.

Although the following description and Examples are primarily directed to the utilization of agglomerated ion exchange cellulose to adsorb and immobilize glucose isomerase, it is also demonstrated that the agglomerated material has the ability to adsorb other proteinaceous material and it is contemplated that the agglomerated material will have the capability of adsorbing other charged macromolecules such as nucleic acids and the like, and further, would be capable of the recovery of such molecules from a variety of substances such as food waste streams, e.g., recovery of protein from milk whey, meat processing streams and vegetable processing streams, reduction of BOD in waste streams, etc.

Due to the high loading capacity of ion exchange cellulose preparations containing glucose isomerase, when such are utilized in industrial applications, relatively small reactors may be employed to convert large quantities of glucose to fructose.

Additionally, because of this high loading capacity, the substrate and the resulting product are maintained under isomerization conditions for only a short period. These isomerization conditions, generally, are conducive to the production of small amounts of unwanted by-products due to the reactive nature of the fructose, and thus, the longer the period the fructose is maintained under such conditions, the greater the amounts of unwanted by-products produced. Thus, the high loading capacity of ion exchange cellulose results in the substrate being isomerized to the desired degree in a short time, thereby decreasing the period during which the fructose component is maintained under isomerization conditions. However, such preparations containing non-granular ion exchange cellulose suffer from the disadvantage of "packing" and, therefore, such are usually utilized in shallow beds to avoid the development of problems due to excessive backpressure. Even when shallow beds are utilized, there is the possibility of channeling occurring whereby the substrate is not contacted to the desired degree with the bound or immobilized glucose isomerase. Although certain immobilized glucose isomerase preparations have been developed to minimize these problems, they generally suffer other disadvantages, e.g., their enzyme capacity or activity per unit volume is not as high as is desired, and/or they are not as economical as ion exchange cellulose.

In practicing the present invention a number of polymers may be utilized to agglomerate the cellulose. Exemplary of these are polymers such as melamine formaldehyde resins, epoxy resins, polystyrene and the like. The preferred polymer is polystyrene.

In U.S. Pat. Nos. 4,110,164 and 4,168,250 it is disclosed that when cellulose which has been derivatized to provide an ion exchange material is agglomerated with a hydrophobic polymer under suitable conditions, such cellulose retains its capacity to immobilize or bind glucose isomerase. The preferred process taught for preparing the composites comprises treating alkali-cellulose with a solution of diethylaminoethyl chloride hydrochloride (DEC) and then agglomerating the derivatized ion exchange cellulose formed thereby with polystyrene. Due to the solubility of polystyrene in the DEC reaction mixture, however, it would be anticipated that the cellulose could not be efficiently derivatized if the agglomerates were formed prior to derivatization of the cellulose.

As mentioned previously, it was discovered by Antrim et al. and disclosed in U.S. Pat. No. 4,335,117 that cellulose can be efficiently derivatized in the presence of the hydrophobic polymer by controlling process conditions during derivatization so as to prevent the polymer from becoming solubilized in the derivatizing solution. Thus, it was found that by adding the derivatizing material at a controlled rate to a water suspension of the agglomerate under alkaline conditions, the hydrophobic polymer component of the granular composite does not become solubilized to a significant degree. When the granular composite is derivatized according to the teachings of U.S. Pat. No. 4,355,117, the granules are derivatized with DEAE at a ratio of DEAE agent to cellulose of greater than 0.7 to impart ion exchange properties thereon.

A further unexpected finding was that when the cellulose was derivatized following agglomeration thereof, the cellulose composite may be derivatized to a higher degree and thus have a greater ion exchange capacity than the agglomerated cellulose composite produced by the process of the prior art wherein the cellulose is derivatized before agglomerization. While the ion exchange capacity of the agglomerated fibrous cellulose composite of that invention may vary widely, typically the ion exchange capacity should be at least about 0.1 meq $g^{-1}$ and preferably at least about 0.2 meq $g^{-1}$.

It has now been surprisingly discovered that following the preparation of the derivatized composite, a treatment thereof with a hot aqueous medium can dramatically increase the adsorption capacity of the composite for charged macromolecules by at least about 30%, more preferably, about 60% to about 100%. By treatment with a hot aqueous medium is meant a treatment at elevated temperatures in a medium such as tap water, deionized water or dilute salt esolutions of up to about 7000 umhos of conductivity, or more preferably up to about 1000 umhos of conductivity. Treatment is at a temperature of about 80° C. to about 100° C. over a time period of about one-half hour to about 5 hours, more preferably, about one-half hour to about 3 hours.

In preparing the composite it is preferred to employ the method of Antrim et al. as described in U.S. Pat. No. 4,355,117, the contents of which are incorporated herein by reference.

Specifically, two types of derivatized granular cellulose were prepared, Type I-GDC contained alumina as a densification agent while Type II-GDC contained titanium dioxide as the densification agent. In preparing each composite the following formulation procedure was used. An agglomerate was prepared by mixing 30 parts CEPO S-100 cellulose (Swedish Cellulose Powder and Woodflower Milk Ltd., Gothenburg, Sweden) and 20 parts of weighting agent (either alumina in the case of Type I or titanium dioxide in the case of Type II) and compounding the mixture with 50 parts polystyrene on a heated (180°-200° C.) twin roll compounder for a period of 10 minutes. After cooling, the compounded composite was ground and sized to 40-80 mesh.

Into one of two 2-liter, four necked pots equipped with stirrer, thermometer with a Therm-0-Water Regulator, condenser, and heating mantle was placed 300 grams of either Type I or Type II granular cellulose ($GC_I$ or $GC_{II}$) and 942 ml of deionized water. With stirring was added 300 grams of anhydrous sodium sulfate, then 82 gms or 50% sodium hydroxide. To each reaction mixture heated to 40° C. was added, using a Technicon Pump, 117 grams of 50% diethylaminoethyl chloride hydrochloride (DEC) reagent. The reagent was added over a two-hour period. The mixture was stirred at 40° C. for 30 minutes, then 62 grams of NaOH was added to each resin and an additional 117 grams of DEC reagent was added over a two-hour period. The reaction mixtures were then heated to 60° C. for approximately 30 minutes, then cooled and the pH adjusted to 6.5 using 30% $H_2SO_4$. The products are designated as granular derivatized cellulose type I ($GDC_I$) and granular derivatized cellulose Type II ($GDC_{II}$).

The granular composites thus prepared may be considered as virgin composites relative to exposure to macromolecular adsorption. That is, a virgin composite, as herein contemplated, is one that has not been previously charged or loaded with such macromolecules.

The following examples illustrate the subject invention but should not be construed to limit same.

EXAMPLE 1

This example illustrates the increase in adsorption capacity for the enzyme glucose isomerase realized when granular derivatized cellulose ($GDC_I$) prepared with alumina weighting agent was treated with water at about 90° C.

Using a U.S. No. 60 mesh stainless steel sieve, 50 g f.b. (fresh basis) of dried $GDC_I$ was screened using about 24 liters of water from a shower head. The screened GDCI was dewatered with a sintered glass funnel and vacuum flask, and then bottled and labeled Sample A.

To 600 ml of deionized water contained in a 1000 ml stainless steel beaker was placed 21.7 g d.b. (dry basis) of the above screened $GDC_I$. The beaker was placed in a water bath heated to about 90° C. and the mixture was stirred in the 90° C. water bath for thirty minutes.

The hot mixture was filtered using a coarse sintered glass funnel and suction flask, and then the GDC solids were placed back into the 1000 ml stainless beaker. To the beaker was added a second 600 ml of deionized water and the mixture was treated with stirring a second time for thirty minutes in the 90° C. water bath.

The hot mixture was filtered as before, and then the GDC solids were treated a third time with 600 ml of deionized water for thirty minutes in the 90° C. water bath. After a final filtration the dewatered, thrice treated $GDC_I$ was bottled and labeled Sample B.

The adsorption capacity of the treated GDC for glucose isomerase was determined using a single point procedure. Thus, into a 140 ml plastic flask with lid was placed 4.835 g f.b. (2.0262 g d.b.) of the treated $GDC_I$ (Sample B) and 50.0 ml of deionized water. To this mixture was added 0.5 ml of 1 M Tris buffer, pH 7.0, and 1.25 ml of glucose isomerase (5412 IGIU/ml) containing 6765 IGIU of activity.

The glucose isomerase may be purified from extracts containing the enzyme by procedures well-known in the art. Such purification procedures include, but are not limited to, centrifugation, salt (e.g. ammonium sulfate) precipitation, and column (e.g., ion exchange or affinity) chromatography.

An International Glucose Isomerase Unit (IGIU) is that amount of enzyme which will convert 1 micromole of glucose to fructose per minute in a solution containing 2 moles glucose, 0.02 moles $MgSO_4$, 0.001 moles $CoCl_2$ per liter at a pH of 6.84 to 6.85 (0.2 M sodium maleate) at a temperature of 60° C.

Sodium chloride was added to give a conductivity of about $9.5 \times 10^3$ umhos and the mixture was agitated 1 hour. The pH was adjusted to 7.1 using dilute HCl and the sample was agitated 4 hours. After settling, a sample of the clear liquid was diluted 1:10 and analyzed via the Technicon Assay as described by Lloyd et al. in Cereal, Chemistry, 49(5), pp. 544-553, (1972). It was found that the clear liquid contained a total of 803 IGIU of glucose isomerase activity. Thus the 2.0262 g d.b. of GDC adsorbed a total of 5960 IGIU of glucose isomerase or 2940 IGIU/g d.b. of $GDC_I$.

Using the same procedure for the starting GDC (Sample A) and the same enzyme, an adsorption capacity of 1955 IGIU/g $GDC_I$ d.b. was obtained. The high temperature treatment thus resulted in a 50% increase in the enzyme adsorption capacity of $GDC_I$.

EXAMPLE 2

This example illustrates the increase in enzyme adsorption capacity realized when granular derivatized cellulose ($GDC_{II}$) prepared with titanium dioxide weighting agent was treated with water at about 90° C.

A 65.5 g f.b. sample (34.5 g d.b.) of $GDC_{II}$ was stirred in a beaker containing about 600 ml of deionized water (room temperature) and then screened using a shower of water, on a U.S. No. 60 mesh stainless steel sieve using about 24 liters of water. The washed GDC was dewatered on a sintered glass funnel, bottled and labeled Sample A. This sample served as a control; there was no 90° C. treatment step.

Another 34.5 g d.b. sample of $GDC_{II}$ was placed, along with 600 ml of deionized water, into a stainless steel beaker. The beaker was placed in a hot water bath at approximately 90° C. and the slurry was stirred at this bath temperature for ½ hour. The resulting product was washed on a U.S. No. 60 mesh stainless steel sieve to remove fines, using about 24 liters of water. The sample was dewatered on a sintered glass funnel, bottled and labeled Sample B.

Another 34.5 g d.b. sample of $GDC_{II}$ was placed, along with 600 ml of deionized water, into a stainless steel beaker and treated as above in the 90° C. water bath for ½ hour. The solids were filtered, resuspended in another 600 ml of deionized water and treated in the 90° C. water bath for ½ hour a second time. The product was washed on a U.S. No. 60 mesh sieve to remove fines and then dewatered using a sintered glass funnel, bottled and labeled Sample C.

Another 34 5 g d.b. sample of $GDC_{II}$ was treated three times with 600 ml portions of deionized water for ½ hour each in the 90° C water bath. The resulting product was then washed on a U.S. No. 60 mesh sieve to remove fines, using about 24 liters of water. The $GDC_{II}$ product was dewatered, bottled and labeled Sample D.

The four GDC products were weighed and analyzed for adsorption capacity of glucose isomerase (GI) enzyme. Results are presented below.

| Sample | A | B | C | D |
|---|---|---|---|---|
| GI Adsorption Capacity (IGIU/g $GDC_{II}$ d.b.) | 2492 | 3455 | 3456 | 3660 |
| Approximate % Increase in Adsorption Capacity | — | 39 | 39 | 47 |

EXAMPLE 3

This example illustrates the adsorption capacity from samples of granular cellulose (GC) first derivatized with varying levels of DEC reagent and then treated with water at about 90° C.

DERIVATIZATION

Into six 2-liter, four necked resin pots equipped with stirrer, thermometer with Therm-0-Watch Regulator, condenser and heating mantle was placed 300 g of standard GDC (compound from polystyrene, CEPO S-100 cellulose and titanium dioxide weighting agent; 50%, 30%, and 20%, respectively, prepared as described above) and 942 ml of deionized water. With stirring was added 300 g of anhydrous sodium sulfate and then 82 g of 50% sodium hydroxide. To each reaction mixture heated to 40° C. was added, using a Technicon Pump, the quantity of 50% diethylaminoethyl chloride hydrochloride (DEC) reagent equivalent to either 50%, 60%, 70%, 80%, 90% or 100% of the standard level of DEC reagent. The 50% DEC reagent was added over a two-hour period.

The reaction mixtures were stirred at 40° C. for 30 minutes and then 62 g of 50% NaOH was added to each resin pot and the second half of the 50% DEC reagent was added over a two-hour period.

The reaction mixtures were heated to 60° C. for approximately 30 minutes and then cooled and the pH was adjusted to 5 using 30% $H_2SO_4$. Presented below are the reaction conditions used for each product.

SCREENING & WASHING

The reaction products were screened through a U.S. No. 30 mesh sieve and collected on a U.S. No. 60 mesh sieve using about 24 liters of water each from a shower head. The product from each reaction (i.e., U.S. #30 to #60 mesh size) was stirred in 2000 ml each of water and washed on a U.S. No. 60 mesh sieve 2000 ml each of water and using the shower head and 24 liters of water. The solids were again dispersed in 2000 ml of water and again washed on the U.S. No. 60 mesh sieve using the shower head and 24 liters of water each. The six reaction products were dewatered on a sintered glass funnel.

HIGH TEMPERATURE TREATMENT

Into 1,000 ml stainless steel beakers were placed 50.0 grams d.b. of each product and 600 ml of deionized water. The beakers were placed in a 90° C. water bath and GDC slurries were stirred for 2 hours at the 90° C. bath temperature. The solids were recovered by hot filtration using a coarse sintered glass funnel and then suspended in 600 ml of deionized water and again stirred for 2 hours in the 90° C. water bath. The resulting hot GDC slurries were filtered using a coarse sintered glass funnel and then the solids were resuspended in 600 ml of deionized water and again stirred for 2 hours in the 90° C. bath. After filtration the thrice treated GDC products were screened on a U.S No. 60 mesh sieve using about 24 liters of water and a shower head. The products were dewatered, and capacity for glucose isomerase measured. Results are presented below:

| | Level of 50% DEC Reagent (%) | | | | | |
|---|---|---|---|---|---|---|
| Sample No. | 100 | 90 | 80 | 70 | 60 | 50 |
| Adsorption Capacity after 90° C. treatment (IGIU/g GDC, d.b.) | 3130 | 2714 | 2538 | 2538 | 2468 | 1953 |

As may be expected the adsorption capacity for glucose isomerase decreased as a function of the DEC reagent level. However, the GDC product prepared using only 60% of the standard level of DEC reagent had an adsorption capacity equivalent to GDC derivatized with 100% of the standard DEC level but not treated at 90° C. See Example 2.

EXAMPLE 4

This example illustrates the effect of treatment temperature on adsorption capacity of GDC.

A 300 g d.b. sample of $GDC_{II}$ was screened and washed on a 60 mesh screen essentially as described in Example 2. The screened GDC was dewatered on a sintered glass funnel and blended thoroughly. Samples

| | | | | 50% NaOH (g) | | 50% DEC Reagent | | |
|---|---|---|---|---|---|---|---|---|
| Exp. No. | Water (g) | GDC (g) | $Na_2SO_4$ (g) | 1st Add'n. | 2nd Add'n. | % of Std. | % 1st Add'n. (g) | % 2nd Add'n. (g) |
| 1 | 942 | 300 | 300 | 82 | 62 | 100 | 117 | 117 |
| 2 | 942 | 300 | 300 | 82 | 62 | 90 | 105 | 105 |
| 3 | 942 | 300 | 300 | 82 | 62 | 80 | 93.6 | 93.6 |
| 4 | 942 | 300 | 300 | 82 | 62 | 70 | 81.9 | 81.9 |
| 5 | 942 | 300 | 300 | 82 | 62 | 60 | 70.2 | 70.2 |
| 6 | 942 | 300 | 300 | 82 | 62 | 50 | 58.5 | 58.5 | of the blended $GDC_{II}$ were taken and suspended in deionized water (10 ml/g d.b.). The samples were stirred for two hours at various temperatures ranging from 50° to 100° C. The $GDC_{II}$s were then collected by filtration on sintered glass funnels. A sample of each $GDC_{II}$ was removed for analysis and the remaining $GDC_{II}$ were resuspended in fresh water for a second two-hour treatment. After the second treatment the $GDC_{II}$s were collected by filtration, sampled for analysis and resuspended in water for a third two-hour treatment. After the third treatment the $GDC_{II}$s were washed with cold water on a 60 mesh screen, dewatered by filtration, and thoroughly blended. The retained samples from the single and double treatments were also screened, dewatered and blended.

The adsorption capacity of each of the above $GDC_{II}$s was determined with glucose isomerase essentially as described in Example 1 except that multiple point adsorptions using varying amounts of $GDC_{II}$ with a constant amount of enzyme were used. Adsorption capacity was calculated by plotting isomerase activity adsorbed vs. weight of $GDC_{II}$ added. The results are summarized in the following table.

ADSORPTION CAPACITIES OF TREATED $GDC_{II}$s

| Treatment Temperature °C. | Number of Treatments | Adsorption Capacity IGIU/g d.b. | Approximate % Increase In Capacity |
|---|---|---|---|
| Control (untreated) | 0 | 2550 | — |
| 50 | 1 | 2465 | −3 |
|  | 2 | 2762 | 8 |
|  | 3 | 2830 | 11 |
| 60 | 1 | 2489 | −2 |
|  | 2 | 2841 | 11 |
|  | 3 | 3303 | 30 |
| 70 | 1 | 2592 | 2 |
|  | 2 | 2756 | 8 |
|  | 3 | 3147 | 23 |
| 80 | 1 | 3058 | 20 |
|  | 2 | 2913 | 14 |
|  | 3 | 3460 | 40 |
| 90 | 1 | 2858 | 12 |
|  | 2 | 3491 | 37 |
|  | 3 | 3438 | 35 |
| 100 | 1 | 4876 | 91 |
|  | 2 | 5216 | 105 |
|  | 3 | 5158 | 102 |

At all temperatures tested adsorption capacity was improved by multiple treatments. The adsorption capacity increased with increasing treatment temperature, such that the adsorption capacity was doubled by two or three treatments at 100° C.

EXAMPLE 5

This example illustrates the effect of high temperature treatment on improving the adsorption capacity of $GDC_{II}$ for a protein other than glucose isomerase.

To determine if the hot water treatment would improve the adsorption capacity for other proteins as well as for glucose isomerase, a 0.2% solution of bovine serum albumin (BSA) (Sigma, Fraction V) was prepared by dissolving the protein in 10 mM Tris buffer, pH 7.0. The conductivity of this solution was adjusted to 9000 umhos by the addition of sodium chloride.

Samples of washed and screened $GDC_{II}$ and of $GDC_{II}$ which had been treated three times at 100° C. as described in Example 4 were used to determine adsorption capacity for BSA. Weighted portions of each $GDC_{II}$ were suspended in 50 ml aliquots of BSA solution and agitated for 60 minutes. The $GDC_{II}$ was allowed to settle by gravity and samples of the clear supernates were taken to determine soluble BAS concentration by ultraviolet absorbance at 280 nm. The adsorption capacity was calculated by difference in the soluble BSA concentration before and after $GDC_{II}$ addition.

The 100° treated $GDC_{II}$ adsorbed 19.7 mg BSA/g d.b. compared to an adsorption of only 11.6 mg BSA/g d.b. for the untreated GDCII Thus, the 100° treatment increased the adsorption capacity for bovine serum albumin by about 70%.

EXAMPLE 6

This example demonstrates the effect of high temperature treatment on other carriers known to adsorb glucose isomerase.

To determine if the improvement in adsorption capacity after hot water treatment of GDC is a general property of isomerase adsorbants, several carriers known to adsorb glucose isomerase were treated for two hours with water at 90° C. Isomerase adsorption capacity was then determined with the untreated and treated carriers. Fibrous DEAE-cellulose (Whatman DE-23), a macroporous polystyrene quaternary amine resin (Amberlite IRA-900, Rohm & Haas), and a macroporous polyphenolic tertiary amine resin (Duolite A-568, Diamond Shamrock) were tested. Ten gram portions of each resin were suspended in 100 ml of deionized water and stirred for two hours at 90° C. The resins were collected and dewatered on sintered glass funnels and portions were used to determine isomerase adsorption capacity essentially as described in Example 4. No difference in isomerase adsorption capacity of the treated vs. untreated carriers was found for IRA-900, IRA-932, or Duolite A-568. The adsorption capacity for Whatman DE-23 was reduced from 3407 IGIU/g for the untreated carrier to 2429 IGIU/g for the treated carrier. Thus, hot water treatment did not improve the adsorption capacity of any of the other non-GDC resins cited.

EXAMPLE 7

This example demonstrates that high temperature treatments with either tap water or dilute salt solution are also effective in increasing adsorption capacity of GDC.

To compare the effect of deionized water, tap water (620 umhos conductivity), and dilute sodium chloride solution (5000 umhos conductivity), samples of GDC II were treated three times at 90° C. with each solution essentially as described in Example 4. The adsorption capacity of the treated GDC's was determined with glucose isomerase, as described in Example 1. The following results were obtained.

| Medium | Adsorption Capacity (IGIU/g d.b.) | Approximate % Increase In Capacity |
|---|---|---|
| None | 2550 | — |
| Deionized Water | 3438 | 35 |
| Tap Water | 3170 | 24 |
| Salt Solution | 4070 | 60 |

Treatment with tap water was almost as effective as treatment with deionized water in increasing GDC adsorption capacity. The dilute salt solution (~0.05 M NaCl) was more effective than either deionized or tap water.

EXAMPLE 8

This example demonstrates the effect of conductivity (salt concentration) on treatment of GDC.

To determine the effect of conductivity on the efficiency of treatment, samples of GDC were treated three times at 100° C. with sodium chloride solutions of various conductivity essentially as described in Example 4. The adsorption capacity of each of the treated GDC's was determined with glucose isomerase, as described in Example 1. The following results were obtained.

| Conductivity (umhos) | Adsorption Capacity (IGIU/g d.b.) | Approximate % Increase In Capacity |
|---|---|---|
| 52 | 4259 | 54 |
| 1000 | 4642 | 69 |
| 3000 | 4260 | 54 |
| 7000 | 3980 | 45 |
| Control (untreated) | 2750 | — |

In all cases the treatment improved the adsorption capacity of the GDC over that of the untreated control. Optimum improvement was seen after treatment with 1000 umhos salt solution (~0.01N NaCl).

What is claimed is:

1. In a process for preparing a grandular composite capable of adsorbing charged macromolecules wherein said composite comprise DEAE-cellulose agglomerated with a hydrophobic polymer, the improvement comprising treating said composite, prior to adsorbing any macromolecules to the composite, with an aqueous medium selected from the group consisting of tap water, deionized water and a dilute salt solution, at a temperature of from about 80° C. to about 100° C., and for a period of time of about one-half hour to about 5 hours, so as to thereby cause an increase in adsorption capacity of the composite of at least about 30% for said macromolecules.

2. The process according to claim 1 wherein said macromolecule is a protein.

3. The process according to claim 2 wherein said protein is an enzyme.

4. The process according to claim 3 wherein said enzyme is glucose isomerase.

5. A granular composite prepared by the process of claim 1.

6. A process as in claim 1 wherein treating is for a period of time of about two hours so as to thereby cause an increase in said adsorption capacity of said composite of about 60% to about 100%.

7. A process as in claim 6 wherein said macromolecule is glucose isomerase.

8. A process as in claim 1 further comprising the step of adsorbing charged macromolecules on said treated composite.

9. A process as in claim 8 in which said macromolecule is a protein.

10. A process as in claim 9 in which said protein is an enzyme.

11. A process as in claim 10 in which said enzyme is glucose isomerase.

12. A process for preparing a granular composite having increased adsorption capacity for charged macromolecules comprising (a) agglomerating a cellulose with a hydrophobic polymer to form a granular composite, (b) derivatizing the agglomerated cellulose in said composite with a DEAE derivatizing agent to impart ion exchange properties thereto, at least a portion of the derivatized cellulose being free to adsorb charged macromolecules, (c) maintaining the derivatized composite in granular form, and (d) prior to adsorbing any macromolecules to said composite, treating the granular derivatized composite with an aqueous medium selected from the group consisting of tap water, deionized water and a dilute salt solution, at a temperature of about 80° C. to about 100° C., for a period of time of about onehalf hour to about 3 hours, so as to thereby cause an increase of at least about 30% in the adsorption capacity of said derivatized composite for said macromolecules.

13. The process according to claim 12 wherein said derivatizing agent is diethylaminoethyl chloride.

14. The process according to claim 12 wherein said hydrophobic polymer is polystyrene.

15. The process according to claim 12 wherein said composite further comprises a densification agent.

16. The process according to claim 12 wherein said densification agent is selected from the group consisting of powdered metal oxides, silicates and mixtures thereof.

17. The process according to claim 16 wherein said densification agent is alumina or titanium oxide.

18. The process according to claim 12 wherein said macromolecule is a protein.

19. The process according to claim 18 wherein said protein is an enzyme.

20. The process according to claim 19 wherein said enzyme is glucose isomerase.

21. A granular composite prepared by the process of claim 12.

22. A process as in claim 12 wherein treating in step (d) is conducted for a period of time of about two hours so as to thereby cause an increase in said adsorption capacity of said composite of about 60% to about 100%.

23. A process as in claim 22 wherein said macromolecule is glucose isomerase.

24. A process as in claim 12 further comprising the step of adsorbing charged macromolecules on said treated composite.

25. A process as in claim 24 in which said macromolecule is a protein.

26. A process as in claim 25 in which said protein is an enzyme.

27. A process as in claim 26 in which said enzyme is glucose isomerase.

28. A granular composite for adsorbing charged macromolecules prepared by steps comprising agglomerating a cellulose with a hydrophobic polymer to form a granular composite, derivatizing said granules with a DEAE derivatizing agent at a ratio of DEAE agent to cellulose of greater than 0.7 to impart ion exchange properties thereof, at least a portion of said derivatized cellulose being free to adsorb charged macromolecules, and, prior to adsorbing any macromolecules to said composite, treating said granules with an aqueous medium selected from the group consisting of tap water, deionized water and a dilute salt solution, at an elevated temperature of from about 80° C. to about 100° C., and for a period of time of about one-half hour to about 5 hours, so as to thereby cause an increase of at least about 30% in adsorption capacity of said composite for said macromolecules.

29. A composite as in claim 28 wherein treating is conducted for a period of time of about two hours so as to thereby cause an increase of about 60% to about 100% in the adsorption capacity of said composite.

30. A composite as in claim 29 in which said macromolecule is glucose isomerase.

31. A composite as in claim 28 further comprising adsorbed charged macromolecules.

32. A composite as in claim 28 in which said macromolecule is a protein.

33. A composite as in claim 32 in which said protein is an enzyme.

34. A composite as in claim 33 in which said enzyme is glucose isomerase.

35. A process for increasing the adsorption capacity of a granular composite for charged macromolecules wherein said composite comprises DEAEcellulose agglomerated with a hydrophobic polymer, which process comprises treating said composite, prior to adsorbing any macromolecules to said composite, with an aqueous medium selected from the group consisting of tap water, deionized water and a dilute salt solution, at a temperature of from about 80° C. to about 100° C., and for a period of time of about one-half hour to about 3 hours, so as to thereby cause an increase of at least about 30% in the adsorption capacity of said composite for said macromolecules.

36. The process according to claim 35 wherein said hydrophobic polymer is polystyrene.

37. The process according to claim 35 wherein said composite further comprises a densification agent.

38. The process according to claim 37 wherein said densification agent is selected from the group consisting of powdered metal oxides, silicates and mixtures thereof.

39. The process according to claim 38 wherein said densification agent is alumina or titanium oxide.

40. The process according to claim 35 wherein said macromolecule is a protein.

41. The process according to claim 40 wherein said protein is an enzyme.

42. The process according to claim 41 wherein said enzyme is glucose isomerase.

43. A process as in claim 35 in which said treating is for a period of time of about two hours so as to thereby cause an increase of about 60% to about 100% in said adsorption capacity of said composite.

44. A process as in claim 43 in which the macromolecules are glucose isomerase.

45. A process as in claim 35 in which said aqueous medium is tap water.

46. A process as in claim 35 in which said aqueous medium is deionized water.

47. A process as in claim 35 further comprising the step of adsorbing charged macromolecules on said treated composite.

48. A process as in claim 47 in which said macromolecule is a protein.

49. A process as in claim 48 in which said protein is an enzyme.

50. A process as in claim 49 in which said enzyme is glucose isomerase.

51. A process for increasing the adsorption capacity of a granular composite for charged macromolecules wherein said composite comprises DEAE-cellulose agglomerated with a hydrophobic polymer which process comprises treating said composite, prior to adsorbing any macromolecules to said composite, with a dilute salt solution, at a temperature of about 80° C. to about 100° C., for a period of time of about one-half hour to about 5 hours, so as to thereby cause an increase of about 45% in the adsorption capacity of said composite for said macromolecules.

52. The process according to claim 51 wherein said salt solution has conductivity of up to about 7000 umhos.

53. The process according to claim 52 wherein said conductivity is up to about 1000 umhos.

54. A process as in claim 51 further comprising the step of adsorbing charged macromolecules on said treated composite.

55. A process as in claim 54 in which said macromolecule is a protein.

56. A process as in claim 55 in which said protein is an enzyme.

57. A process as in claim 56 in which said enzyme is glucose isomerase.

* * * * *

UNITED STATES PATENT AND TRADEMARK OFFICE
CERTIFICATE OF CORRECTION

PATENT NO. : 5,001,063
DATED : March 19, 1991
INVENTOR(S) : Richard L. Antrim, et al.

It is certified that error appears in the above-identified patent and that said Letters Patent is hereby corrected as shown below:

Column 8, lines 8 & 9: delete "2000 ml each of water and"

Column 12, line 16: "onehalf" should read as --one-half--

Signed and Sealed this

Twenty-seventh Day of October, 1992

Attest:

DOUGLAS B. COMER

*Attesting Officer*  *Acting Commissioner of Patents and Trademarks*